(12) United States Patent
Yoshida et al.

(10) Patent No.: US 12,343,187 B2
(45) Date of Patent: Jul. 1, 2025

(54) X-RAY IMAGING EQUIPMENT

(71) Applicant: SHIMADZU CORPORATION, Kyoto (JP)

(72) Inventors: Koki Yoshida, Kyoto (JP); Dai Hirose, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 241 days.

(21) Appl. No.: 17/984,109

(22) Filed: Nov. 9, 2022

(65) Prior Publication Data

US 2023/0210483 A1    Jul. 6, 2023

(30) Foreign Application Priority Data

Jan. 6, 2022  (JP) .................. 2022-001145

(51) Int. Cl.
  *A61B 6/00* (2024.01)
  *A61B 6/42* (2024.01)

(52) U.S. Cl.
  CPC .............. *A61B 6/4441* (2013.01); *A61B 6/42* (2013.01)

(58) Field of Classification Search
  CPC ... A61B 6/4464; A61B 6/4476; A61B 6/4441; A61B 6/035; A61B 6/42; A61B 6/0487; A61B 6/40; A61B 6/4435; A61B 6/487; A61B 6/54; A61B 6/0407; A61B 6/589; A61B 5/055; A61B 5/704; A61B 6/4417; A61B 6/0442; A61B 6/0457; A61B 6/467; A61B 6/547; A61B 6/102; A61B 6/485; A61B 6/4458; A61B 6/587; A61B 6/463; A61B 6/4452; A61B 6/4405; A61B 6/08; A61B 6/14; A61B 6/145; A61B 6/542; A61B 6/032; A61B 6/466; A61B 6/5205; A61B 6/5223; A61B 6/027; A61B 6/4233; A61B 6/5241; A61B 6/06; A61B 6/405; A61B 6/512; A61B 6/51; A61B 6/02; A61B 6/03; A61B 6/4208; A61G 13/02; A61G 13/04; A61G 13/06; A61G 13/10; A61G 13/104; A61G 2210/50; B25J 9/00; G06F 3/01; G06T 15/005; G06T 15/08; G06T 7/0012; Y02B 90/2692; Y02B 90/20
  USPC .......................................................... 378/63
  See application file for complete search history.

(56) References Cited

U.S. PATENT DOCUMENTS

2007/0253539 A1* 11/2007 Noda ................... A61B 6/4464
                                                                 378/197
2010/0054423 A1*  3/2010 Noda ................... A61B 6/4464
                                                                 378/197

FOREIGN PATENT DOCUMENTS

JP       2020-08140 A     6/2020

* cited by examiner

*Primary Examiner* — Irakli Kiknadze
(74) *Attorney, Agent, or Firm* — Andrew F. Young, Esq.; Nolte Lackenbach Siegel

(57) ABSTRACT

An X-ray imaging apparatus reduces waiting time and smoothly performs position alignment with a target region. The X-ray imaging apparatus has a C-arm that supports an X-ray tube and an X-ray detector; a turning mechanism that turns the C-arm around the vertical axis AX2; a table on which a subject M is loaded; a console; and a control element, wherein the control element runs the turning mechanism to turn the C-arm in the direction toward the preset target angle when the console provides the input power to perform the relative move of the table relative to the C-arm.

9 Claims, 10 Drawing Sheets

*FIG. 5*

|  | AT1 | AT2 | AT3 |
|---|---|---|---|
|  | Manual ON | Manual OFF | Electric operation |
| Brake 53, 67 | OFF | ON | OFF |
| Clutch 51, 65 | OFF | OFF | ON |

X-RAY IMAGING EQUIPMENT

CROSS REFERENCE TO RELATED APPLICATION

This application relates to, and claims priority from, Ser. No.: JP2022-001145 filed Jan. 6, 2022, the entire contents of which are incorporated herein by reference.

FIGURE FOR PUBLICATION

FIG. 1.

BACKGROUND OF THE INVENTION

Field of the Invention

The present invention relates to an X-ray fluoroscopic imaging apparatus.

Description of the Related Art

A conventional X-ray imaging apparatus comprises an X-ray imaging apparatus main body and an examination table. The X-ray imaging apparatus main body comprises a C-shaped arm (C-type arm) having an X-ray tube and an X-ray detector at both ends and an arm turning mechanism. The arm turning mechanism performs the turning movement to turn the C-shaped arm around the vertical axis while supporting the C-shaped arm. The examination table comprises a table movable in the horizontal direction.

The X-ray imaging apparatus main body stands by the location on the line extending from the body axis of a subject on the head-side of the subject (patient) loaded on the table. At this time, the C-shaped arm, the X-ray detector (the X-ray tube) and the table are arrayed in order on the linear line in the planar view.

When trying to access a target region (such as the groin) of the subject in such a situation, an operator feels that the operation is cumbersome if the operator runs individually the moving operations of the C-shaped arm and the table. Then, it has a structure in which the C-shaped arm automatically turns when the table moves to the preset region. (Refer to e.g., Patent Document 1)

RELATED PRIOR ART

Patent Document 1 JP 2020-081410 A1

ASPECTS AND SUMMARY OF THE INVENTION

Objects to be Solved

However, here are following problems in the conventional X-ray imaging apparatus. According to Patent Document 1, the timing when the turning movement of the C-shaped arm starts is after the table travels the predetermined distance. Therefore, there is the case in which the operator should hold running the turning movement of the C-shaped arm to align the position to e.g., the groin of the subject.

In addition, the C-shaped arm having the X-ray tube and the X-ray detector is large and heavy, so that it is difficult to carry out any quick turning movement. Further, even if any quick turning movement could be carried out, it is afraid of that the equipment placed in the surrounding area of the C-shaped arm and other staff member clash with such as the C-shaped arm. Therefore, only increase of the turning speed is not preferable to address the above problem.

Considering such circumstances, the object of the present invention is to provide an X-ray imaging apparatus capable of cutting the time for holding (waiting) and performing smoothly position alignment with the target region.

Means for Solving the Problem

The present invention constitutes the following structure to achieve such a purpose. Specifically, an X-ray imaging apparatus of the present invention comprises:
a C-shaped arm that supports an X-ray tube and an X-ray detector;
a turning mechanism that turns the C-shaped arm around the vertical axis;
a table on which a subject is loaded;
an operation element; and
a control element, wherein
the control element turns the C-shaped arm in the direction toward the preset target angle by running the turning mechanism when the operation element provides an input power to perform a relative move of the table relative to the C-shaped arm.

According to the X-ray imaging apparatus of the present invention, the C-shaped arm is turned in the direction toward the preset target angle by running the turning mechanism when the operation element provides the input power to perform the relative move of the table relative to the C-shaped arm. Specifically, regardless the length of the distance between the table and the C-shaped arm, the input power to perform the relative move relative to the C-shaped arm performs the turning movement of the C-shaped arm in the direction toward the target angle. Accordingly, the timing to start the turning movement of the C-shaped arm in the direction toward the target angle can be set early, so that the holding (waiting) time for the turning movement of the C-shaped arm can be reduced. Accordingly, the position alignment with the target region can be performed smoothly.

Effects of the Present Invention

According to the X-ray imaging apparatus of the present invention, the holding (waiting) time decreases and the position alignment with the target region can be performed smoothly.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 5 is an explanatory drawing to explain respective operations of a table operation switch, an electric horizontal movement switch and four direction keys.

DETAILED DESCRIPTION OF THE PREFERRED EMBODIMENTS

Figure 1:
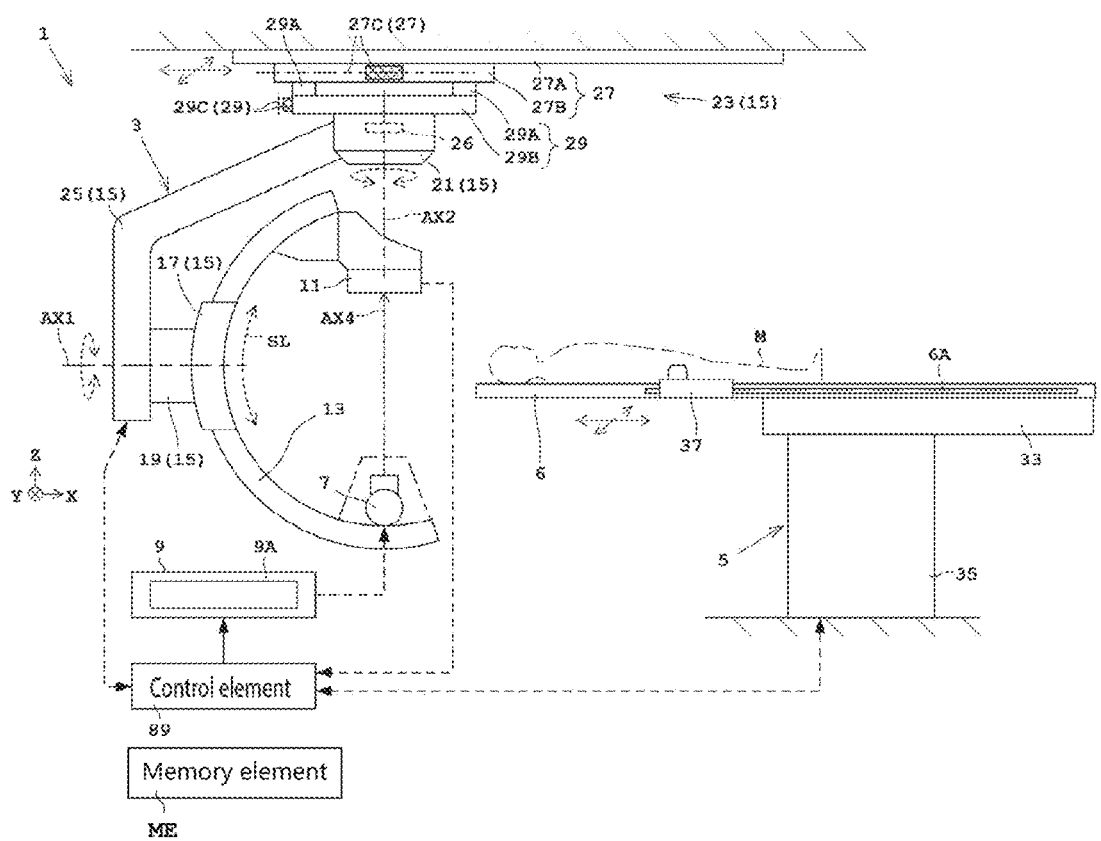
FIG. 1 is a side view illustrating the X-ray imaging apparatus according to the Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Referring to Figures, the inventor sets forth Embodiments of the present invention for an X-ray imaging apparatus.

Embodiment 1

Figure 2:
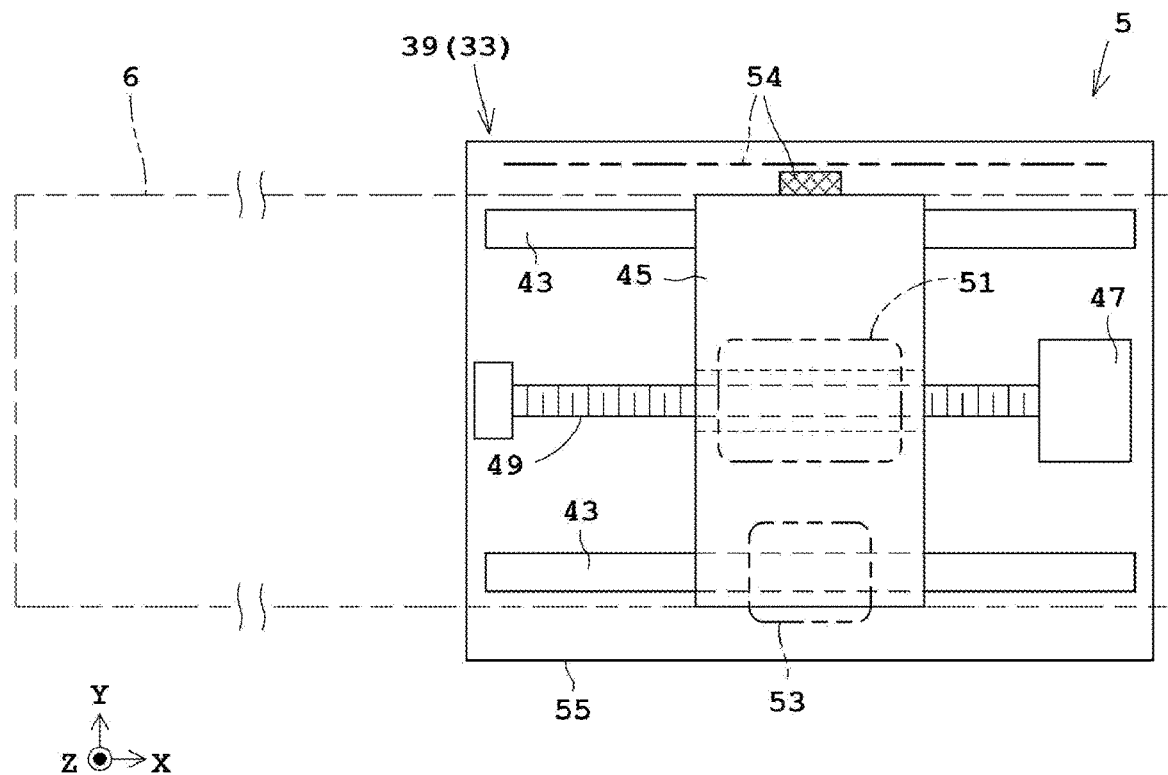
FIG. 2 is a plan view illustrating the X-moving element of a table horizontal movement mechanism.
Figure 3:
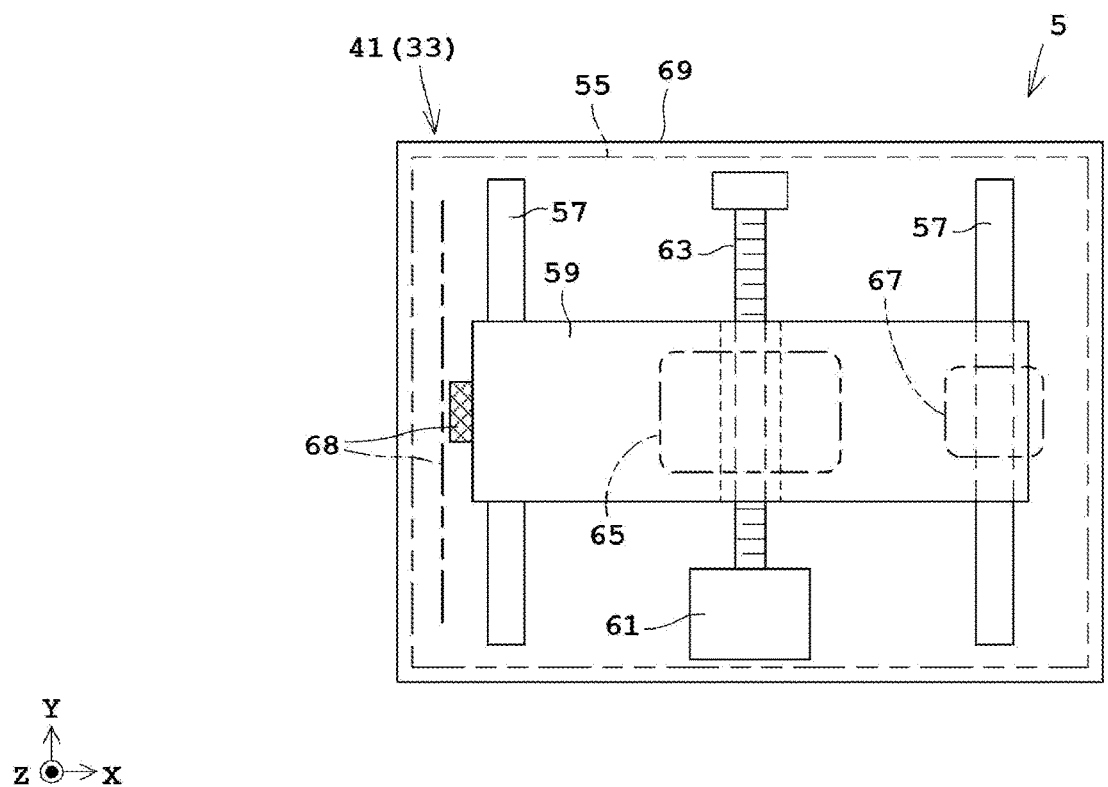
FIG. 3 is a plan view illustrating the Y-moving element of the table horizontal movement mechanism.

FIG. 1 is a side view illustrating the X-ray imaging apparatus according to the Embodiment 1. FIG. 2 is a plan view illustrating the X-moving element 39 of the table horizontal movement mechanism 33. FIG. 3 is a plan view illustrating the Y-moving element 41 of the table horizontal movement mechanism 33.

(1) Structure of the X-Ray Imaging Apparatus

Referring to FIG. 1. The X-ray imaging apparatus 1 comprises the X-ray imaging apparatus main body 3 and the examination table 5. The examination table 5 comprises a table 6 on which the subject M is loaded. The inventors set forth the detail of the examination table 5 later. The X-ray imaging apparatus main body 3 comprises the X-ray tube 7, an X-ray tube control element 9 and the X-ray detector 11. The X-ray tube 7 irradiates the X-rays to the subject M loaded on the table 6. The X-ray tube 7 is controlled by the X-ray tube control element 9. The X-ray control element 9 comprises a high voltage generation unit 9A and supplies the X-ray tube 7 with the preset tube voltage and the tube electric current. A collimator (not shown in FIG.) that adjusts an X-ray exposure field is mounted in the X-ray tube 7.

The X-ray detector 11 is in place facing the X-ray tube 7 and detects the X-ray transmitting the subject M. The X-ray detector 11 comprises an FPD (Flat Panel Detector) consisting of an X-ray conversion layer (film). In addition, the X-ray detector 11 may further comprise an image intensifier and a camera. The X-ray detector 11 outputs an X-ray image obtained based on the detected X-ray. The X-ray image output therefrom is displayed on a monitor, not shown in FIG., (e.g., a liquid crystal display and an organic EL (electro-luminescence) display).

The X-ray imaging apparatus main body 3 further comprises the C-shaped arm (here, called "C-arm" arbitrarily) 13 and a C-arm driving mechanism 15. The C-arm 13 supports the X-ray tube 7 and an X-ray detector 11 at both ends thereof. The C-arm 13 is formed so as to have a C-like shape. In addition, the shape (appearance) of the C-arm includes a letter C like shape and a letter U like shape. Further, the C-arm can be configured to have the letter C like shape formed of three linear column members.

The C-arm driving mechanism 15 supports the C-arm 13 so as to be movable and also drives the C-arm 13. The C-arm driving mechanism 15 further comprises a sliding mechanism 17, a horizontal axis rotation mechanism 19, a turning mechanism 21 and a horizontal movement mechanism 23.

The sliding mechanism 17 supports the C-arm 13 so as to be movable and also slides (rotates) the C-arm 13 along the C-shape (pathway) of the C-arm 13 as shown as the (broken line) arrow sign SL in FIG. 1. The horizontal axis rotation mechanism 19 supports the sliding mechanism 17 so as to be rotatable around the horizontal axis AX1 extending in parallel to the plane formed as the letter C like shape according to the C-arm 13. Further, the horizontal axis rotation mechanism 19 rotates the C-arm 13 and the sliding mechanism 17 around the horizontal axis AX1.

The turning mechanism 21 supports the horizontal axis rotation mechanism 19 so as to be rotatable around vertical axis AX2 by the supporting member 25 formed as approximately letter L like shape. Further, the turning mechanism 21 turns the C-arm 13, the sliding mechanism 17 and the horizontal axis rotation mechanism 19 around the vertical axis AX2. The sliding mechanism 17, the horizontal axis rotation mechanism 19 and the turning mechanism 21 have an electric motor respectively. The sliding mechanism 17, the horizontal axis rotation mechanism 19 and the turning mechanism 21 are driven by the respective electric motors. The turning mechanism 21 comprises an angle sensor 26 detects a turning angle of the C-arm 13 around the vertical axis AX2. The angle sensor 26, for example, is a rotary encoder.

The horizontal movement mechanism 23 moves such as the C-arm 13 in the horizontal direction (XY-direction). The horizontal movement mechanism 23 comprises an X-moving element 27 and Y-moving element 29. The X-moving element 27 comprises two guide rails 27A, a movable member 27B, a X-position sensor 27C and an X-driving element (not shown in FIG). The guide rails 27A are in place as extending in the X-direction and fixed on the ceiling of the examination room. The guide rails 27A support a movable member 27B so as to be movable in the X-direction. The movable member 27B is moved in the X-direction by the X-driving element while being guided by the guide rails 27A. The X-driving element and the Y-driving element, which is described later, respectively comprise an electric motor. Further, the X-driving element and the Y-driving element, which is described later, respectively comprise, for example, a screw axis or a ball screw. The X-position sensor 27C detects the position of the movable member 27B (C-arm 13) in the X-direction. The X-position sensor 27C and the Y-position sensor 29C (later described) are respectively, for example, a linear encoder or a rotary encoder.

The Y-moving element 29 comprises two guide rails 29A, the movable member 29B, the Y-position sensor 29C and the Y-driving element (not shown in FIG). The guide rails 29A are in place so as to be extending in the Y-direction and mounted to the X-movable member 27B of the X-moving element 27. The guide rails 29A support the movable member 29B so as to be movable in the Y-direction. The movable member 29B is moved in the Y-direction by the Y-driving element while being guided by the guide rails 29A. The turning mechanism 21 is installed under the movable member 29B. The Y-position sensor 29C detects the position of the movable member 29B (C-arm 13) in the Y-direction.

The examination table 5 comprises the table 6, the table horizontal movement mechanism 33, a pedestal 35 and a console (operation panel) 37. The table horizontal movement mechanism 33 supports the table 6 so as to be movable in the horizontal direction and also moves the table 6 in the horizontal direction (XY-direction). The table horizontal movement mechanism 33 comprises an X-moving element 39 and Y-moving element 41 referring to FIG. 2 and FIG. 3.

Referring to FIG. 2. The X-moving element 39 comprises two guide rails 43, the movable member 45, the electric motor 47, the screw axis 49, the X-clutch 51, an X-brake 53, the X-position sensor 54 and a mount member 55. The table 6 is fixed to the movable member 45. The guide rails 43 supports the movable member 45 so as to be movable in the X-direction. Therefore, the table 6 is moved along with the movable member 45 in the X-direction. In addition, the guide rails 43 are in place so as to be extending in the X-direction. The screw axis 49 connects to the output rotation axis of the electric motor 47. The X-clutch 51 and the X-brake 53 are installed to the movable member 45.

The X-clutch 51 transmits the electric power from the electric motor 47 to the movable member 45 or does not, while changing rotation of the screw axis 49 to the linear movement in the X-direction. The X-clutch 51 comprises, for example, a clutch member formed of internal threads (a female screw) and a clutch driving element (e.g., solenoid or electric motor). In addition, for example, the internal threads engage with not less than half part of the external threads of the screw axis 49. The X-clutch 51 engages the internal threads with the screw axis 49 and cancels such an engagement by that the clutch driving member driving element pushes the clutch member to the screw axis 49 or pulls away from the screw axis 49.

The X-brake 53 can push a piece of the brake to, for example, the guide rail 43. The X-brake 53 locks the movable member 45 (table 6) not to move in the X-direction or releases the locked state thereof. The X-position sensor 54 detects the position of the movable member 45 (table 6) in the X-direction. The X-position sensor 54 and the Y-position sensor 68 (later described) are respectively, for example, linear encoders. The guide rail 43 and the electric motor 47 are installed to the flat mount member 55.

Referring to FIG. 3. The Y-moving element 41 is in place under the X-moving element 39. The Y-moving element 41 comprises two guide rails 57, the movable member 59, the electric motor 61, the screw axis 63, the Y-clutch 65, the Y-brake 67, the Y-position sensor 68 and the mount member 69. The mount member 55 of the X-moving element 39 is fixed to the movable member 59. The guide rails 57 supports the movable member 59 so as to be movable in the Y-direction. Therefore, the table 6 and the mount member 55 (X-movement element 39) move along with the movable member 59 in the Y-direction. In addition, the guide rails 57 are in place so as to be extending in the Y-direction. The screw axis 63 connects to the output rotation axis of the electric motor 61. The Y-clutch 65 and the Y-brake 67 are installed to the movable member 59.

The Y-clutch has the same structure as the X-clutch 51. The Y-clutch 65 transmits the electric power from the electric motor 61 to the movable member 59 or does not, while converting the rotation of the screw axis 63 to the linear movement in the Y-direction. The Y-brake 67 has the same structure as the X-brake 53. The Y-brake 67 locks the movable member 59 (table 6) not to move in the Y-direction or releases the locked state thereof. The Y-position sensor 68 detects the position of the movable member 59 (table 6) in the Y-direction. The guide rail 57 and the electric motor 61 are installed to the mount member 69.

In addition, two sets of the guide rails, 43, 57 and the two movable members 45, 59 form the table support element. In addition, at least two electric motors 47, 61 are corresponding to the vertical driving element of the present invention. In addition, the console 37 corresponds to the operation element of the present invention.

The pedestal 35 supports the table horizontal movement mechanism 33, i.e., the mount member 69. The pedestal 35 is fixed on the floor surface of the examination room. In addition, the pedestal 35 may comprise the table 6 and a table lifting mechanism that lifts the table horizontal movement mechanism 33. In such a case, the lifting mechanism comprises an electric motor to lift the table 6.

(1-1) Configuration of the Console 37

The console 37 is applied to operate the examination table 5, which includes the table 6, and the X-ray imaging apparatus main body 3. The console 37 is mounted to the table 6. Specifically, the rail 6A is installed to the side surface of the long side of the table 6 (referring to FIG. 1). The console 37 is mounted to the rail 6A above. In such way, the console 37 is movable integrally with the table 6.

Figure 4:
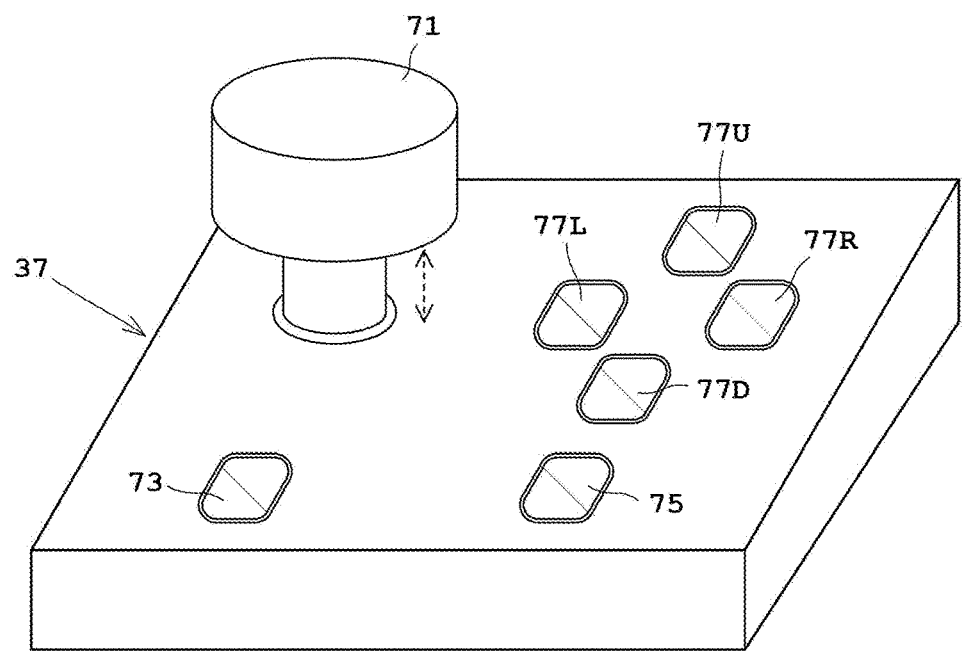
FIG. 4 is a perspective view illustrating a console.

Referring to FIG. 4, the console 37 comprises a plurality of switches 71, 73, 75, 77U, 77D, 77L and 77R. Specifically, the console 37 comprises the table operation switch 71, the mode selection switch 73, the electric power horizontal operation switch 75 and the direction keys 77U, 77D, 77L and 77R. Each switch comprises a button member and an elastic body.

The table operation switch 71 is the switch to perform the manual horizontal movement operation of the table 6. The manual operation is the operation, for example, in which an operator performs to push and pull the table 6 without using the two electric motors 47, 61 (horizontal driving element). The mode selection switch 73 is the switch to select the femoral approach mode (specific imaging mode) to observe, for example, the groin region of the subject.

In addition, the preset target region of the present invention in advance is not limited to the groin region. For example, when the relative movement between the table 6 and the C-arm 13 is performed, the region of the subject M, for which turning of the C-arm 13 is required, can be included in the preset target region. The mode selection switch 73 corresponds to the mode selection element of the present invention.

The electric power horizontal operation switch 75 is the switch to empower the two electric motors 47, 61 (horizontal driving element) to run the operation of the table 6. When the operation of the table 6 is empowered by pushing the electric power horizontal operation switch 75, the respective direction keys 77U, 77D, 77L, 77R are switches to move the table 6 using any one of the two electric motors 47, 61.

The direction key 77U allows the table 6 to move in the +Y-direction. The direction key 77D allows the table 6 to move in the −Y-direction. In addition, the direction key 77L allows the table 6 to move in the −X-direction. The direction key 77R allows the table 6 to move in the +X-direction. When the direction keys 77U, 77D, 77L, 77R are not particularly distinguished, it is called (collectively) the direction keys 77.

Here, referring to FIG. 5, the inventors set forth respectively the table operation switch 71, the electric horizontal movement switch 75 and four direction keys 77.

First, when the two brakes 53, 67 are in the ON state together, the table 6 is locked in the XY-direction. Whereas, when the two brakes 53, 67 are in the OFF state together, the table 6 is not locked in the XY-direction. In addition, the two clutches 51, 65 are in the ON state together, the internal screw of the clutch member of the X-clutch 51 engages with the screw axis 49 and also the internal screw of the clutch member of the Y-clutch 65 engages with the screw axis 63. Whereas the two clutches 51, 65 are in the OFF state together, the clutch member of the X-clutch 51 is away from the screw axis 49 and also the clutch member of the Y-clutch 65 is away from the screw axis 63.

Referring to FIG. 5, the examination table 5 is usually in the state indicated by the sign AT2. At this time, when the table operation switch 71 is pushed, the two brakes 53, 67 are in the "OFF state" and also the two clutches 51, 65 are in the "OFF state" as indicated by the sign AT1. Such states are being kept while the table operation switch 71 is being pushed. When the table operation switch 71 is freed at the state indicated by the sign AT1, the two brakes 53, 67 are in the "ON state" and also the two clutches 51, 65 are in the "OFF state" as indicated by the sign AT2.

Further, when the electric power horizontal operation switch 75 is pushed while in the sign AT2 state and then after, for example, when one of two direction keys 77L, 77R is pushed, the X-brake 53 is in the "OFF state" and also the X-clutch 51 is in the "ON state" as indicated by the sign AT3. In addition, for example, when the direction key 77L is pushed, the table 6 is moved to the C-arm 13 side (−X-direction) as shown in FIG. 1 by the electric motor 47 (horizontal driving element). Further, when the direction key 77L is freed, it turns back to the sign AT2 state.

Further, when one of two direction keys 77U, 77D is pushed, the Y-brake 67 is in the "OFF state" and also the Y-clutch 65 is in the "ON state". Further, for example, when the direction key 77U is being pushed, the table 6 is moved in the +Y-direction by the electric motor 47 (horizontal driving element). Further, when the direction key 77U is freed, it turns back to the sign AT2 state.

Rereferring to FIG. 1 The X-ray imaging apparatus 1 comprises a control element 89 and a memory element ME. The control element 89 controls each component element of the X-ray imaging apparatus 1. The control element 89 comprises, for example, one or more processors such as a central processing unit (CPU). The memory element ME comprises at least one memory selected from a group consisting of, for example, ROM (read only memory), RAM (random access memory) and a hard-disk drive but not limited. The memory element ME stores computer programs to control respective components of the X-ray imaging apparatus.

(2) Operation of the X-Ray Imaging Apparatus 1

Figure 6:
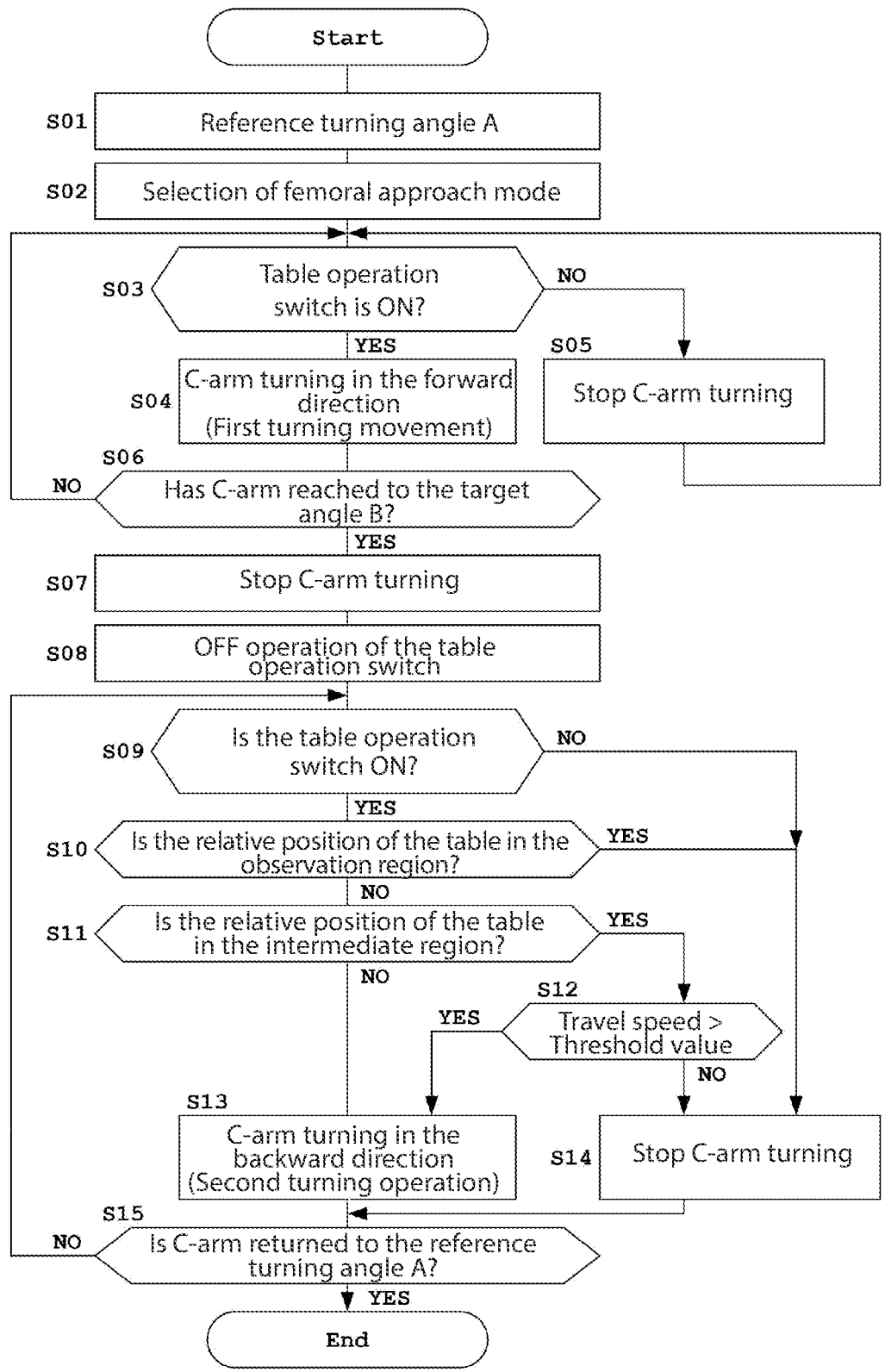
FIG. 6 is a flow chart illustrating an operation of the X-ray imaging apparatus according to the Embodiment 1.

Next, referring to the flow chart illustrated in FIG. 6, the inventors set forth an operation of the X-ray imaging apparatus 1. In addition, FIG. 7, FIG. 8 are schematic views illustrating an operation of the X-ray imaging apparatus 1.

[Step S01] Reference Turning Angle A

Figure 7:
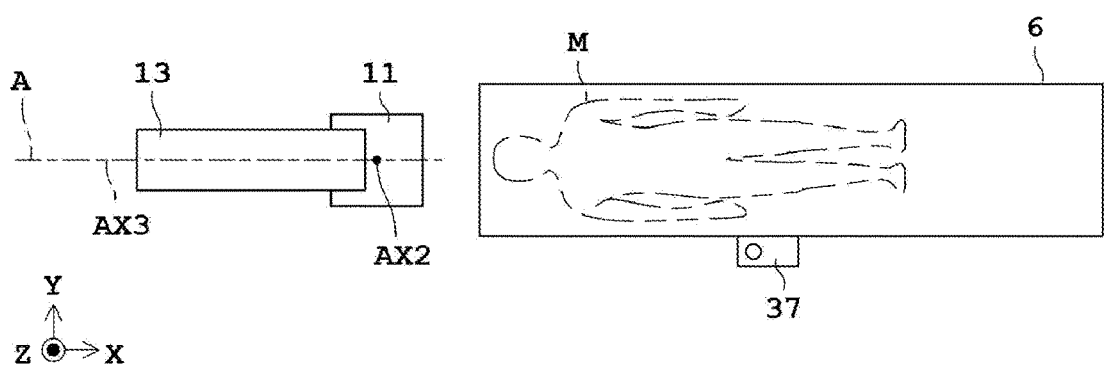
FIG. 7 is a plan view illustrating the X-ray imaging apparatus when the turning angle of the C-arm is a reference turning angle.
Figure 8:
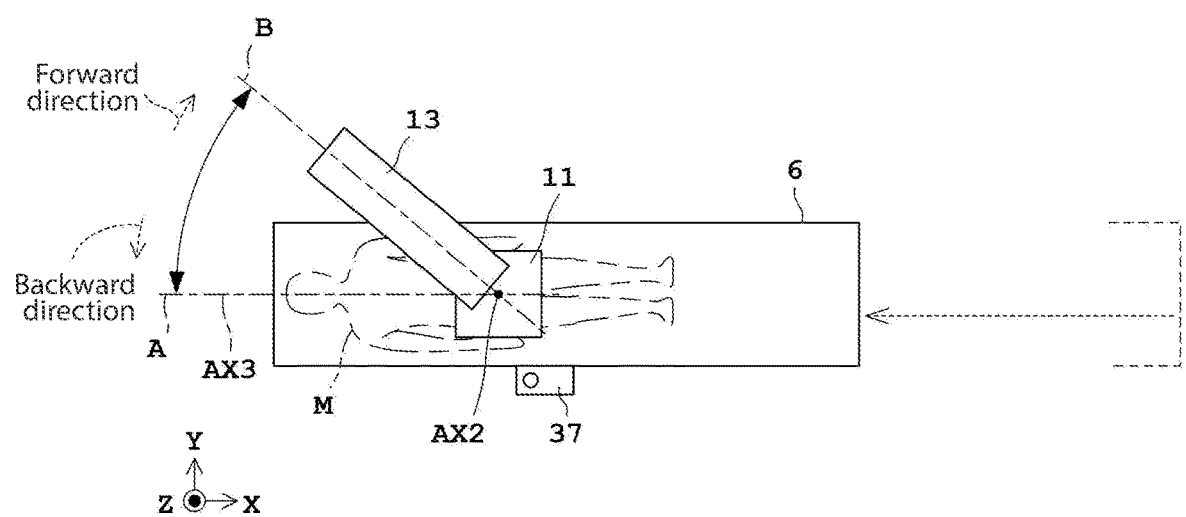
FIG. 8 is a plan view illustrating the X-ray imaging apparatus when the turning angle of the C-arm is the target angle.

Referring to FIG. 7, the C-arm 13 is in place in the head side of the subject M (patient) loaded on the table 6. The C-arm 13 is stationed in the reference position (home position) by the C-arm driving mechanism 15 and has two reference postures. The inventors specifically set forth. Referring to FIG. 7, it is provided that the reference axis AX3 is parallel to the long side direction of the table 6. The C-arm 13 is adjusted to take the first reference position, in which the C-arm 13 is parallel to the reference axis AX3, by the turning mechanism 21 (referring to FIG. 1). At this time, the turning angle given by the turning mechanism 21 is called the "reference turning angle A" or the reference turning position A.

In addition, referring to FIG. 7, the C-arm 13 is adjusted to take the second reference position (center position) by the sliding mechanism 17 and the horizontal axis rotation mechanism 19 so that the X-ray axis AX4 (center axis of the X-ray beam referring to FIG. 1) connecting the X-ray tube 7 and the X-ray detector 11 is parallel to the vertical axis AX2. Specifically, the C-arm 13 has the X-ray tube 7 and the X-ray detector 11 that are in place vertically. In such a case, a part of the C-arm 13 in the X-ray tube 7 side is overlapped with a part of the C-arm 13 in the X-ray detector 11 side. The X-ray tube 7 is in place in the downside of the X-ray detector 11 in the second reference position. In addition, the position of the C-arm 13 in the horizontal direction is adjusted in the reference position by the horizontal movement mechanism 23.

[Step S02] Selection of Femoral Approach Mode

Referring to FIG. 7, the subject M is loaded on the table 6 of the examination table 5. The operator pushes the selection switch 73 installed to the console 37 to observe the target region (e.g., groin region) of the subject M on the table 6. Followingly, the control element 89 controls the X-ray imaging apparatus 1 according to the femoral approach mode. Specifically, the control element 89 controls the apparatus according to Step S03-Step S15 provided the femoral approach mode is selected. On the other hand, if the femoral approach mode is not selected, it is not controlled according to Step S03-Step S15. For example, even if the table operation switch 71 is pushed, the C-arm 13 is not turned interlockingly.

[Step S03-S08] Turning Operation of the C-Arm 13 from the Reference Turning Angle A to the Target Angle B in the Forward Direction And then after, the operator pushes the table operation switch 71 to move manually (by a human power) the table 6 on which the subject M is loaded. Followingly, the table operation switch 71 is in the ON state ("YES" of Step S03). In addition, the table operation switch 71 is pushed, so that the input power to move the table 6 can be provided.

When the table operation switch 71 is pushed, the two brakes 53, 67 are in the "OFF state" and also the two clutches 51, 65 are in the "OFF state" as indicated by the sign AT1 in FIG. 5. Specifically, when the table operation switch 71 is pushed (i.e., the input power to move the table 6 is given), the control element 89 cancels the locked state of the table 6 by the two brakes 53, 63. Subsequently, the state in which the operator manually enables moving the table 6 is obtained. In addition, moving manually the table 6 means that the table 6 is moved without using the two electric motors 47, 61 (horizontal driving element).

Further, the control element 89 performs the first turning operation in which the locked state of the table 6 is canceled and also the C-arm 13 is turned toward the preset target angle B by running the turning mechanism 21 when the table operation switch 71 is pushed (Step S03, S04). Specifically, the control element 89 synchronizes canceling the locked state of the table 6 and starting the first turning operation. The target angle B is an angle corresponding to the reference turning angle A. The target angle B is e.g., 40° (referring to FIG. 8). The target angle B is also called the target position B.

Further, when the table operation switch 71 is freed on the way traveling from the reference turning angle A to the target angle B, i.e., the pushing state, in which the table operation switch 71 is being pushed, is canceled, the control element 89 suspends the first turning operation of the C-arm 13 in synchronism with locking the table 6 (referring to Step S03, S05, Sign AT2 in FIG. 5). Specifically, when the C-arm has not yet reached to the target angle B and the table operation switch 71 is freed, the control element 89 locks the table 6 and also stops (suspends) the first turning operation of the C-arm 13. In addition, when the table operation switch 71 is freed, the table operation switch 71 is in the OFF state. In addition, the table operation switch 71 is freed, the input power can be provided to inhibit moving the table 6.

Then after, when the table operation switch 71 is pushed again, the control element 89 cancels the locked state of the table 6 and also takes up the first turning operation of the C-arm 13 using the turning mechanism 21 (referring to the sign AT1, and Step S03, S04 in FIG. 5).

If the table operation switch 71 is pushed continuously, the state in which the table 6 can be manually moved in the horizontal direction and the first turning operation of the C-arm 13 from the reference turning angle A to the target angle B are continuously functioning. When the C-arm 13 attains the target angle B, the control element 89 suspends the first turning operation of the C-arm 13 using the turning mechanism 21 (Step S06, S07). As a result, even when the table operation switch 71 is being further pushed continuously, the turning mechanism 21 does not turn the C-arm to have the larger turning angle than the target angle B (e.g., 40°).

The operator performs manually the table operation until getting the groin region of the subject M in the radiation field of the X-ray tube 7. When the manual table operation is completed, the table 6 is locked by freeing the table operation switch 71 (referring to the sign AT2 in FIG. 5 and Step S08). Then after, the operator performs at least one operation selected from a group consisting of the X-ray fluorescence imaging and the X-ray imaging using the X-ray imaging apparatus to insert a catheter by making a puncture in the groin region. In addition, when the table operation switch 71 is freed after the C-arm 13 attains the target angle B, the X-ray imaging apparatus 1 changes the state thereof from the state of moving to the target angle B to the state of returning to the reference turning angle A.

[Step S09-S15] Turning Operation of the C-Arm from the Target Angle B to the Reference Turning Angle A in the Backward Direction.

Step S09-S15 are steps in which the C-arm 13 returns from the target angle B to the reference turning angle A. First, referring to FIG. 9, the inventors set forth the region R0 to which the relative position Px of the table 6 relative to the C-arm 13 moves in the long side direction of table 6. The relative position Px of the table 6 is obtained from the difference between the absolute position of the C-arm 13 in the X-direction, which is detected by the X-position sensor 27C (referring to FIG. 1), and the absolute position of the table 6 in the X-direction, which is detected by the X-position sensor 54. The region R0 is divided into the observation region R1, the intermediate region R2 and the waiting region R3.

The observation region R1 is the region where the target region of the subject M such as the groin region is observed. The observation region R1 is the region where the relative position Px of the table 6 exists when the distance between the table 6 and the C-arm 13 is short. For example, the operator performs the X-ray fluoroscopy relative to the groin region of the subject M, the relative position Px of the table 6 exists in the observation region R1.

The waiting region R3 is an outside region of the observation region R1. The waiting region R3 is the region where the relative position Px of the table 6 exists when the distance between the table 6 and the C-arm 13 is long. The intermediate region R2 is the region between the observation region R1 and the waiting region R3.

Figure 9:
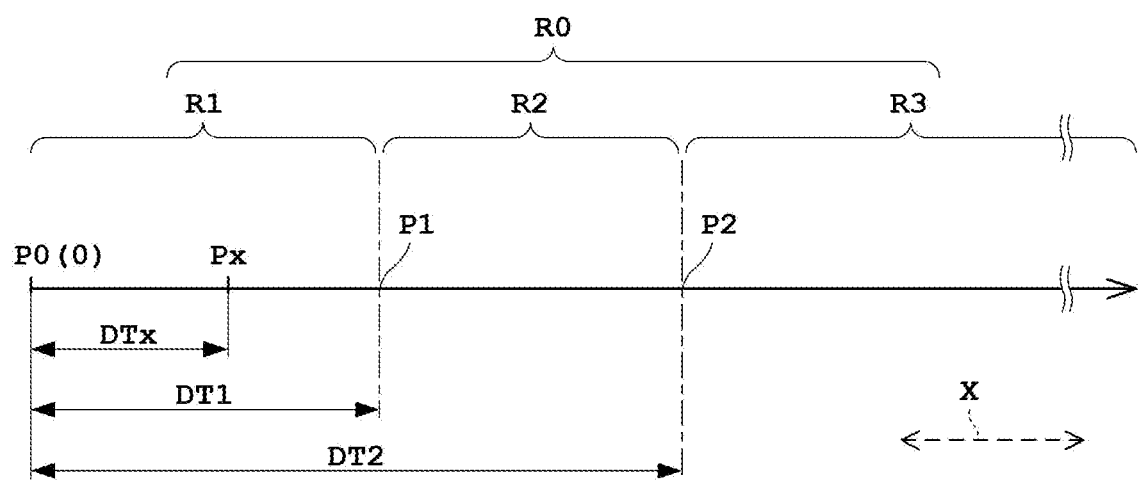
FIG. 9 is a diagram illustrating an observation region, an intermediate region and a holding region.

In addition, referring to FIG. 9, the sign P0 is the absolute position of the C-arm 13 and also the origin of the local coordinate system. The sign P1 is the boundary region between the observation region R1 and the waiting region R2. The sign P2 is the boundary region between the intermediate region R2 and the waiting region R3. The sign DTx is the distance between the C-arm 13 and the table 6. The sign DT1 is the distance between the absolute position P0 of the C-arm 13 and the boundary position P1. The sign DT2 is the distance between the absolute position P0 of the C-arm 13 and the boundary position P2.

The turning movement (second turning movement) of the C-arm 13 in the backward direction is performed provided the table operation switch is in the state of ON (Step S09) and in addition, the condition based on the relative position Px of the table 6 in the X-direction is satisfactory (Step S10-S12). The inventors set forth specifically.

After conducting the X-ray fluoroscopy, the operator moves the table 6, on which the subject M is loaded, manually in the direction (at least +X-direction) in which the table 6 is moving away from the C-arm 13 while pushing the table operation switch 71 (YES in Step S09). Further, right after the X-ray fluoroscopy is performed, the relative position Px of the table 6 exists in the observation region R1. In such a case, the turning movement of the C-arm 13 in the backward direction is not performed (Step S10, S14).

When the relative position Px of the table 6 exists in the intermediate region R2, it is decided whether the moving speed of the table 6 in the +X-direction is higher than the preset value (threshold value) or not (Step S11, S12). When the moving speed of the table 6 in the direction (+X-direction) from the observation region R1 to the waiting region R3 is higher than the threshold value, the control element 89 turns the C-arm 13 in the opposite (backward) direction of the forward direction which is the direction toward the target angle B (Step S11, S12, S13). In addition, when the moving speed is lower than the threshold value, the turning movement of the C-arm 13 in the backward direction is not performed (Step S11, S12, S14). Because the intension of the operator, by which the table 6 is assuredly returned to the waiting region R3, is not recognized.

The relative position Px of the table 6 exists in the waiting region R3, the turning movement in the backward direction is performed (NO in Step S10, NO in Step S11 and Step S13) is performed regardless the moving speed of the table 6 indicated at Step S12. The turning movement in the backward direction is ongoing provided the conditions of Step S09, S10, S1, S12 are satisfactory.

When the table operation switch 71 is freed on the way traveling from the target angle B to the reference turning angle A, i.e., the state in which the table operation switch 71 is being pushed is canceled, the control element 89 locks the table 6 and also stops (suspends) the turning operation of the C-arm 13 in the backward direction (Step S09, S14). Further, the turning movement in the backward direction is performed continuously until returned to the reference turning angle A.

According to the present Embodiment, the state of that the table 6 is ready to be moved manually is set by canceling the locked state of the table 6 and also the C-arm 13 is turned in the direction toward the preset target angle B by running the turning mechanism 21 when the input power to perform moving the table 6 relative to the C-arm 13 from the console 37 is provided. Specifically, regardless the length of the distance between the table 6 and the C-arm 13, the turning movement of the C-arm 13 in the direction toward the target angle B is performed. Accordingly, the timing to start the turning movement of the C-arm 13 in the direction toward the target angle B can be set as an earlier time, so that the holding (waiting) time for the turning movement of the C-arm 13 can be reduced. Accordingly, the position alignment with the target region can be performed smoothly.

Embodiment 2

Figure 10:
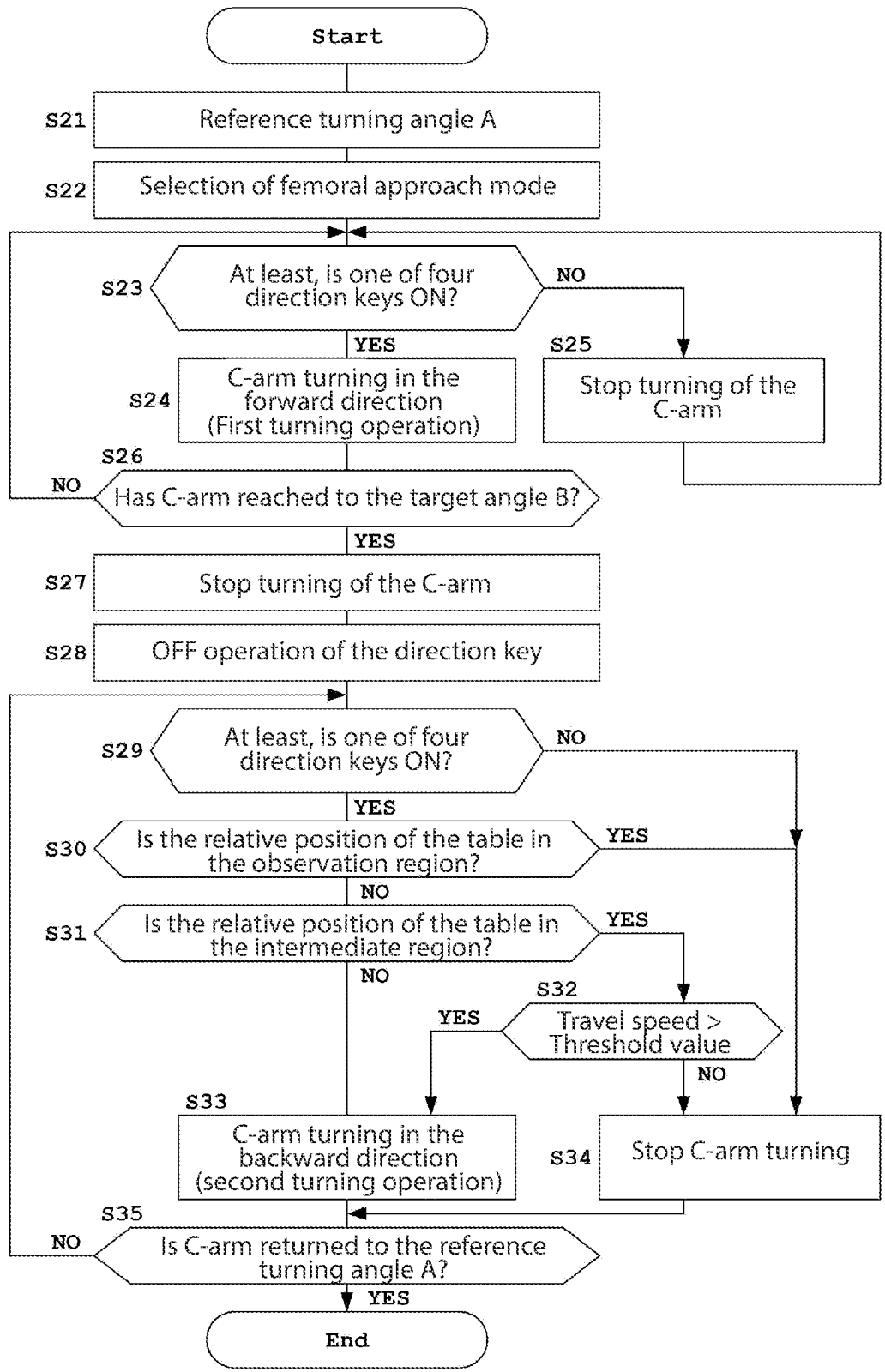
FIG. 10 is a flow chart illustrating an operation of the X-ray imaging apparatus according to the Embodiment 2.

Next, referring to FIGs, the inventors set forth the Embodiment 2 of the present invention. In addition, the description that is overlapping Embodiment 1 is skipped. FIG. 10 is the flow chart illustrating the X-ray imaging apparatus 1 according to the aspect of the Embodiment 2.

According to the Embodiment 1, when the table operation switch 71 is pushed, the state in which the table 6 can be moved manually is in place and also the turning movement (first turning operation) of the C-arm 13 in the forward direction is performed. In such a way, according to the present embodiment, when one of the four direction keys 77A-77D (referring to FIG. 4) to move the table 6 using an electric power, the table is moved using the electric power and also the turning movement of the C-arm 13 is performed in the forward direction.
(3) Operation of the X-Ray Imaging Apparatus 1

Referring to FIG. 10, the inventors set forth an operation of the X-ray imaging apparatus 1 of the present embodiment. Steps S21, S22 referring to FIG. 10 are the same as Step S01, S02 illustrated in FIG. 6. The operator pushes the mode selection switch 73 at Step S22. Followingly, the control element 89 performs controls according to Step S23-S35
[Step S23-S28] Turning Operation of the C-Arm from the Reference Turning Angle A to the Target Angle B in the Forward Direction.

And then after, the operator pushes the electric horizontal switch 75 to move the table 6 using the electric power (two electric motors 47, 61), on which the subject M is loaded. Followingly, the control element 89 allows the table 6 to be moved in the horizontal direction using the four direction keys 77.

And then after, the operator pushes one of four direction keys 77. For example, provided the direction key 77L is pushed, the pushed direction key is in place in the "ON state" (YES in Step S23). Further, when the direction key 77L is pushed, the X-brake 53 is in place in the "OFF state" and the X-clutch 51 is in place in the "ON state" (referring to the sign AT3 in FIG. 5). Further, when the direction key 77L is pushed, the control element 89 runs the electric motor 47 to move the table 6 in the −X-direction (horizontal direction).

Further, when the direction key 77L is pushed, the control element 89 moves the table 6 in the −X-direction and also performs the turning movement of the C-arm 13 in the forward direction by running the turning mechanism 21 (Step S23, S24). Specifically, the start of movement of the table 6 in the −X-direction in the forward direction and the start of the turning movement are synchronized to each other. Further, while pushing the direction key 77L, the control element 89 performs moving the table 6 and also the turning movement of the C-arm 13 in the forward direction. In addition, for example, when pushing the direct key 77U, moving the table 6 in the +Y-direction and also the turning movement of the C-arm 13 are performed.

Further, when all keys 77 are freed on the way from the reference turning angle A to the target angle B, the control element 89 suspends moving the table 6 in the horizontal direction using the two electric motors 47, 61 (sign AT2 in FIG. 5, "NO" in Step S23). Further, the control element 89 suspends moving the table 6 in the horizontal direction and also stops (suspends) the turning movement of the C-arm 13 in the forward direction (Step S23, S25). And then after, when pushing one of the four direction keys 77, the control element 89 reinstates moving the table 6 and also running the turning movement of the C-arm 13 in the forward direction. In addition, when freeing the direction key 77L, the direction key 77L is in place in the OFF state. Specifically, the input power is provided to inhibit moving the table 6 by freeing the table operation key 77.

When the angle around the vertical axis AX2 of the C-arm 13 attains the target angle B, the control element 89 suspends the turning operation of the C-arm 13 in the forward direction (Step S26, S27). Specifically, even when pushing continuously each direction key 77, the horizontal movement operation of the table 6 can be performed but the turning mechanism 21 does not turn the C-arm 13 to have the larger turning angle than the target angle B. In addition, after the C-arm 13 attains the target angle B and in addition when all direction keys 77 are freed, the X-ray imaging apparatus 1 changes the state thereof from the state of moving to the target angle B to the state of returning to the reference turning angle A (Step S28).
[Step S29-S35] Turning Operation of the C-Arm from the Target Angle B to the Reference Turning Angle A in the Backward Direction.

Step S29-S35 are steps in which the C-arm returns from the target angle B to the reference turning angle A. After conducting such as the X-ray fluoroscopy, the operator moves the table 6, on which the subject M is loaded, with the electric power in the direction in which the table 6 goes away from the C-arm 13 by pushing one of the four direction keys 77 ("YES" in Step S29).

The turning movement (second turning movement) of the C-arm 13 in the backward direction is performed provided one of the four direction keys 77 is in place in the state of ON (Step S29) and in addition, the condition based on the relative position Px of the table 6 is satisfactory (Step S30-S32). The relative position Px is the relative position of the table 6 relative to the C-arm 13 in the long side direction (X-direction). Further, as well as the embodiment 1, the region R0, to which the relative position Px of the table 6 moves, is divided into the observation region R1, the intermediate region R2 and the waiting region R3 (referring to FIG. 9). When the relative position Px of the table 6 exists in the observation region R1, at least one electric motor selected from a group consisting of the electric motors 47, 61 conducts the movement of the table 6 in the horizontal direction but not the turning movement of the C-arm 13 in the backward direction (second turning movement) (Step S30, S34).

Further, when the relative position Px of the table 6 exists in the intermediate region R2 and the moving speed of the table 6 in the direction toward the waiting region R3 from the observation region R1 (+X-direction) is higher than the preset value, the turning movement of the C-arm 13 in the backward direction is performed by the turning mechanism 21 (Step S31, S32, S33). Further, when the relative position Px of the table 6 exists in the intermediate region R2 but the moving speed of the table 6 in the +X-direction is lower than the preset value, the turning movement of the C-arm 13 in the backward direction is not performed by the turning mechanism 21 (Step S31, S32, S34).

Further, the relative position Px of the table 6 exists in the waiting region R3, the turning movement of the C-arm 13 in the backward direction is performed regardless the moving speed of table 6 (NO in Step S30, NO in Step S31 and Step S33). The turning movement in the backward direction is ongoing provided the conditions of Step S29, S30, S31, S32 are satisfactory.

When all direction keys 77 are freed on the way from the target angle B to the reference turning angle A, the control element 89 stops (suspends) the horizontal movement of the table 6 and the turning movement of the C-arm 13 in the backward direction using the two electric motors 47, 61 (Step S29, S34). Further, the turning movement in the backward direction is performed continuously until returning to the reference turning angle A.

According to the present embodiment, when the console 37 provides the input power to move the table 6 relative to the C-arm 13, at least one electric motor selected from a group consisting of the electric motors 47, 61 is run to move the table 6 in the horizontal direction, and also the C-arm 13 is turned in the direction toward the preset target angle B by running the turning mechanism 21. Specifically, regardless the length of the distance between the table 6 and the C-arm 13, the turning movement of the C-arm 13 in the direction toward the target angle B is performed. Accordingly, the timing to start the turning movement of the C-arm 13 in the direction toward the target angle B can be set as an earlier time, so that the holding (waiting) time for the turning movement of the C-arm 13 can be reduced. Accordingly, the position alignment with the target region can be performed smoothly.

The present invention is not limited to the aspect of the Embodiments set forth above and another alternative Embodiment can be implemented set forth below.

(1) According to the Embodiment 2 described above, for example, when pushing one of the direction keys 77, the control element 89 moves the table 6 in the horizontal direction and also performs the turning movement of the C-arm 13 in the forward direction. From this standpoint, when pushing one of the direction keys 77, the control element 89 may move the C-arm 13 in the horizontal direction by running the horizontal movement mechanism 23 and also perform the turning movement of the C-arm 13 in the forward direction by running the turning mechanism 21. Specifically, the start of movement of the C-arm 13 in the horizontal direction and the start of the turning movement of the C-arm 13 may synchronize to each other.

In such a way, when pushing one of the direction keys 77 to move the C-arm 13 in the horizontal direction, the input power to perform the relative move of the table 6 relative to the C-arm 13, i.e., the input power to move the C-arm 13 in the horizontal direction is provided.

According to such an alternative embodiment, the operation of the X-ray imaging apparatus is performed as Step S21-S35 illustrated in the flow chart referring to FIG. 10 of the embodiment 2. For example, after the turning angle of the C-arm 13 attains the target angle B and when one of the direction keys 77 is pushed and the relative position Px of the table 6 (i.e., the relative position of the C-arm 13 relative to the table 6 in the X-direction) is in place in the waiting region R3, the control element 89 turns the C-arm 13 in the backward direction (NO for Step S30 of FIG. 10, NO of Step S31 and Step S33).

In such an alternative embodiment, the console 37 may further comprise four direction keys to move the C-arm 13 in the horizontal direction. In addition, the four direction keys 77 are not only used to move the table 6 in the horizontal direction but also may be used to move the C-arm 13 in the horizontal direction. In such a case, the console 37 may comprise a switch allowing the four direction keys 77 to be used to move the C-arm 13 in the horizontal direction.

(2) According to each embodiment described above, the relative position Px, which is the distance between the position of the C-arm 13 in the X-direction, which is detected by the X-position sensor 27C, and the position of the table 6 in the long side direction (X-direction), which is detected by the X-position sensor 54, is used to decide the condition to perform the turning movement of the C-arm 13 in the backward direction. In such a way, when moving the table 6, the absolute position of the table 6 in the X-direction detected by the X-position sensor 54 may be used. Further, when moving the table 13, the absolute position of the table 13 in the X-direction detected by the X-position sensor 27C may be used.

(3) The respective embodiments and alternative embodiment (1) described above may be configured as follows. Referring to FIG. 6, the turning movement of the C-arm 13 in the backward direction is performed provided the table operation switch is ON (Step S09) and in addition, the condition based on the long side direction of the table 6 is satisfactory (Step S10-S12). From this standpoint, for example, each decision as to S10, S11, S12 can be skipped.

Specifically, after the turning angle of the C-arm 13 attains the target angle B, when the table operation switch 71 is in place in OFF and then after the table operation switch 71 is returned ON, the control element 89 may cancel the locked state of the table 6 and also run the turning movement of the C-arm 13 in the backward direction. However, if the condition of the turning movement of the C-arm 13 in the backward direction is only the incident in which the table operation switch 71 turns the ON state (Step S09), the unexpected turning movement of the C-arm 13 in the backward direction may take place regardless the intension of the operator. Therefore, the three region R1, R2, R3 are set up and Step S10-S12 are included, so that the turning movement that the operator does not intend can be prevented. In addition, in the case illustrated FIG. 10, each decision as to S30, S31, S32 may be skipped.

(4) According to the respective embodiments and alternative embodiments described above, the control element 89, turns the C-arm 13 in either forward or backward direction, for example, based on the state in which the table operation switch is ON (Step S04, S13). When turning the C-arm 13, the control element 89 may perform the control as follows. Specifically, when the X-ray axis AX4 connecting the X-ray tube 7 and the X-ray detector 11 tilts around the horizontal axis AX1 relative to the vertical axis AX2, the control element 89 may turn the C-arm 13 in the forward or backward direction following rotating the C-arm 13 around the horizontal axis AX so that the X-ray axis AX4 is parallel to the vertical axis AX2.

Further, the control element 89 may rotate the C-arm 13 around the horizontal axis AX1 and turn the C-arm 13 following sliding the C-arm 13 along the shape C of the C-arm 13 so that the X-ray axis AX4 is parallel to the vertical axis AX2 by running the horizontal axis rotation mechanism 19 and the sliding mechanism 17 when the X-ray axis AX4 tilts relative to the vertical axis AX2 in the case of turning the C-arm 13 based on the state in which the table operation switch 71 is in place ON.

In addition, referring to FIG. 1, the X-ray imaging apparatus main body 3 may not need to comprise at least one mechanism selected from the group consisting of the sliding mechanism 17 and the horizontal axis rotation mechanism 19. For example, if the X-ray imaging apparatus main body 3 does not have the horizontal axis rotation mechanism 19, the control element 89 may perform the following control. Specifically, the control element 89 turns the C-arm 13 following sliding the C-arm 13 along the shape C of the C-arm 13 so that the X-ray axis AX4 is parallel to the vertical axis AX2 by running the sliding mechanism 17 when the X-ray axis AX4 tilts relative to the vertical axis AX2 in the case of turning the C-arm 13 based on the state in which the table operation switch 71 is in place in the ON state.

According to such an operation, for example, the operation such as the collision of the table 6 and C-arm 13, which the operator does not intend, can be prevented. It is considered as the same case in which the C-arm is tuned in the Step S24, S33 referring to FIG. 10.

(5) According to the respective embodiments and alternative embodiments described above, the horizontal movement mechanism 23 (including the guide rails 27A) of the X-ray imaging apparatus main body 3 is installed to the ceiling of the examination room. Specifically, the X-ray imaging apparatus main body 3 is the apparatus main body which travels on the ceiling. From this standpoint, the X-ray imaging apparatus main body 3 can be the apparatus main body installed on the floor. In such a case, the horizontal movement mechanism 23 in FIG. 1 may be installed on the floor of the examination room. Further, the horizontal movement mechanism 23 installed on the floor is not limited to have the two sets of guide rails 27A, 29A and e.g., may have a Scala type multi-joint arm.

(6) According to the respective embodiments and alternative embodiments described above, the examination table 5 is capable of operating the table 6 selectively by using the manual operation or the electric power operation. From this standpoint, the examination table 5 is not capable of operating the table 6 by using the electric power of two electric motors 47, 61 but may be capable of operating the table 6 manually. In such a case, the table horizontal movement mechanism 33 may not have the two electric motors 47, 61, the two screw axes 49, 63 and the two clutches 51, 65 referring to FIG. 2. FIG. 3. Further, the console 37 referring to FIG. 4 may not have the electric power horizontal operation switch 75 as to the electric operation and the four direction keys 77.

Further, the examination table 5 is not capable of operating the table 6 manually but may be capable of operating electrically by using the two electric motors 47, 61. In such a case, the movable member 45 referring to FIG. 2 may have a nut instead of the X-clutch 51, which always engages with the screw axis 49. Further, the movable member 59 referring to FIG. 3 may have a nut instead of the Y-clutch 65, which always engages with the screw axis 63. Further, the console 37 referring to FIG. 4 may not have the table operation switch 71 relative to the manual operation.

(7) According to the respective embodiments and alternative embodiments described above, the X-ray imaging apparatus 1 may be configured to perform both Steps S03-S15 referring to FIG. 6 and Steps S23-S35 referring to FIG. 10. For example, when moving the table 6 manually following pushing the mode selection switch 73, the control element 89 performs controls according to the Steps S03-S15. Further, when moving the table 6 using the electric power, the control element 89 performs controls according to Steps S23-S35.

(8) According to the respective embodiments and alternative embodiments, Steps S08-S15 referring to FIG. 6 can be skipped as needed. Further, referring to FIG. 10, Steps S28-S35 can be skipped as needed. Specifically, the control element 89 may perform the turning movement of the C-arm 13 in the forward direction without performing the turning movement of the C-arm 13 in the backward direction.

(9) According to the respective embodiments and alternative embodiments described above, when pushing the table operation switch 71 and one direction key 77, the input power to move the table 6 relatively is provided. Further, when freeing the table operation switch 71 and the instant one direction key 77 respectively, the input power to inhibit the movement of the table 6 is provided. The input power is not limited thereto. The table operation switch 71 and the four direction keys 77 can be switches capable of respectively selecting one of two kinds of the input power. In addition, when the console 37 comprise a touch panel and a monitor (e.g., liquid crystal display), at least one of a plurality of the switches 71, 73, 75, 77 can be a switch capable of being displayed on the monitor.

(10) According to the respective embodiments and alternative embodiments described above, the console 37 is configured to move together with the table 6. From this standpoint, the console 37 and the table 6 can be separately in place so that the console 37 and the table 6 would not move in a unified manner.

(11) According to the embodiment 2 and each alternative embodiment described above, when pushing one of the direction keys 77, the control element 89 moves the table 6 with the electric power and also performs the turning movement of the C-arm 13 in the forward direction. From this standpoint, when simultaneously pushing the two direct keys 77 (e.g., direction keys 77D, 77L), the control element 89 may move the table 6 in the predetermined horizontal direction using the electric power and also perform the turning movement of the C-arm 13 in the forward direction. It is considered as the same case in which the C-arm 13 is turned in the reverse (backward) direction.

(12) According to the respective embodiments and alternative embodiments described above, the region R0, to which the relative position Px of the table 6 (or the C-arm 13) moves, is divided to the observation region R1, the intermediate region R2 and the waiting region R3. From this standpoint, the region R0 may be divided to the observation region R1 and the waiting region R3.

(Effects of the Aspect of Embodiment)

Hereinafter, the inventors set forth the configuration of the X-ray imaging apparatus 1 and the effect thereof according to the aspect of the present embodiment.

(1) The X-ray imaging apparatus 1, according to the present embodiment, comprises: the C-arm 13 that supports the X-ray tube 7 and the X-ray detector 11; the turning mechanism 21 that turns the C-arm 13 around the vertical axis AX2; the table 6 on which the subject M is loaded; the operation element (console) 37, and the control element 89, wherein the control element 89 runs the turning mechanism 21 to turn the C-arm 13 in the direction toward the preset target angle B when the input power to perform the relative move of the table 6 relative to the C-arm 13 by the operation element 37.

According to the X-ray imaging apparatus 1 above described, the C-arm 13 is turned in the direction toward the preset target angle B by running the turning mechanism 21 when an input power to perform the relative move of the table 6 to the C-arm 13 is provided by the operation element 37. Specifically, regardless the length of the distance between the table 6 and the C-arm 13, the turning movement of the C-arm 13 in the direction toward the target angle B is performed by the input power to perform the relative move relative to the C-arm 13 performs. Accordingly, the timing to start the turning movement of the C-arm 13 in the direction toward the target angle B can be set as an earlier time, so that the holding (waiting) time for the turning movement of the C-arm 13 can be reduced. Accordingly, the position alignment with the target region can be performed smoothly.

(2) The X-ray imaging apparatus 1 above described, further comprises: the mode selection element (mode selection switch) 73 that selects the specific imaging mode (femoral approach mode) to observe the preset target region of the subject M, wherein the C-arm 13 is turned in the direction toward the preset target angle B by running the turning mechanism 21 when an input power to perform the relative move of the table 6 relative to the C-arm 13 is provided by the operation element 37 based on the condition in which the mode selection element 73 selects the specific imaging mode by the mode selection element. Specifically, the turning movement of the C-arm 13 in the direction toward the preset target angle B is not performed even when the input power to perform the relative move of the table 6 relative to the C-arm 13 is provided from the operation element (console) 37. Accordingly, the turning movement of the C-arm 13 can be performed only as needed.

(3) According to the X-ray imaging apparatus 1 described above, when after the turning angle of the C-arm 13 attains the target angle B and the input power to perform the relative move of table 6 is provided, and when the relative position Px of the table 6 relative to the C-arm 13 in the long side direction of the table 6 is in the waiting region R3 outside the observation region R1 to observe the preset target region of the subject M, the control element 89 performs turning the C-arm 13 in the opposite direction of the direction toward the target angle B by running the turning mechanism 21. For example, when the relative position Px is in the observation region R1, the turning movement of the C-arm 13 in the opposite direction is not performed. Therefore, the turning movement that the operator does not intend can be prevented.

(4) According to the X-ray imaging apparatus 1 described above, when after the turning angle of the C-arm 13 attains the target angle B and the input power to perform the relative move of table 6 is provided and when the relative position Px of the table 6 in the intermediate region R2 between the observation region R1 and the waiting region R3, and the moving speed of the table 6 from the observation region R1 to the waiting region R3 is higher than the preset value, the control element 89 performs turning the C-arm 13 in the opposite direction of the direction toward the target angle. Therefore, without returning the relative position Px of the table 6 until the waiting region R3, for example, when the intension to assuredly return the table 6 to the original position of the waiting region R3 is read, the turning operation in the backward (opposite) direction is performed. Therefore, the turning movement that the operator does not intend can be prevented.

(5) According to the imaging apparatus 1 described above, the control element 89 suspends the turning operation of the C-arm 13 by the turning mechanism 21 when an input power to inhibit the relative move of the table 6 is provided by the operation element 37. Therefore, the turning operation such as a collision of table 6 and C-arm 13, which the operator does not intend, can be prevented.

(6) The imaging apparatus 1 described above, further comprises: the horizontal axis rotation mechanism 19 that rotates the C-arm 13 around the horizontal axis AX1; wherein when the C-arm 13 is turned based on providing the input power to perform the relative move of the table 6 and the X-ray axis AX4 connecting the X-ray tube 7 and the X-ray detector 11 tilts relative to the vertical axis AX2, the control element 89 turns the C-arm 13 following running the horizontal axis rotation mechanism 19 to rotate the C-arm 13 around the horizontal axis AX1 so that the X-ray axis AX4 is parallel to the vertical axis AX2. After the horizontal axis rotation mechanism 19 reinstates the reference position in which the X-ray tube 7 and the X-ray detector are aligned in the vertical direction, the turning movement of the C-arm 13 is performed. Therefore, the rotation and turning movement that the operator does not intend can be prevented.

(7) According to the imaging apparatus 1 described above, the control element 89 cancels the locked state of the table 6 and provides the state in which the table 6 can be manually moved and also turns the C-arm 13 when the input power to perform moving the table 6 from the operation element 37 is provided. Therefore, the position alignment with the target region can be performed smoothly when the table 6 is moved manually. Further, if the table 6 is moved manually, the position alignment can be performed faster than the case in which the table 6 is moved by using the horizontal driving element (two electric motors 47, 61).

(8) The imaging apparatus 1 described above, further comprises: the horizontal driving element (47, 61) that move the table 6 in the horizontal direction; wherein when the input power to move the table 6 by the operation element 37 is provided, the control element 89 runs the horizontal driving element (47, 61) to move the table 6 in the horizontal direction and also turn the C-arm 13. Therefore, the position alignment with the target region can be performed smoothly when the horizontal driving element (47, 61) moves the table 6.

(9) The X-ray imaging apparatus 1 described above, further comprises: the horizontal movement mechanism 23 that moves the table 6 in the horizontal direction, the control element 89 runs the horizontal movement mechanism 23 to move the C-arm 13 in the horizontal direction and turn the C-arm 13 when an input power to perform moving the table 6 is provided by the operation element 37. Accordingly, the position alignment with the target region can be performed smoothly when moving the C-arm 13 using the horizontal movement mechanism 23.

REFERENCE DESIGNATOR LISTING

1 X-ray imaging apparatus
6 Table
7 X-ray tube
11 X-ray detector
13 C-arm (C-shaped arm)

15 C-arm driving mechanism
19 Horizontal axis rotation mechanism
21 Turning mechanism
23 Horizontal movement mechanism
27C, 54 X-position sensor
33 Table horizontal movement mechanism
37 Console (Operation element)
43, 57 Guide rail
45, 59 Movable member
47, 61 Electric motor
53 X-brake
67 Y-brake
71 Table operation switch
73 Mode selection switch
77 (77U, 77D, 77L, 77R) Direction key
89 Control element
AX1 Horizontal axis
AX2 Vertical axis
AX4 X-ray axis Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray imaging apparatus, comprising:
a C-shaped arm that supports an X-ray tube and an X-ray detector;
a turning mechanism that turns said C-shaped arm around a vertical axis;
a memory element that stores a target angle about turning of said C-shaped arm around said vertical axis;
a table on which a subject is loaded;
a table horizontal movement mechanism that moves said table in a horizontal direction,
a switch that receives operation by an operator, and
a control element; wherein
said control element,
reads out said target angle to be stored in said memory element;
allows said table horizontal movement mechanism to move said table in said horizontal direction or causes said table horizontal movement mechanism to move said table in said horizontal direction and turns said C-shaped arm in a direction toward said target angle read out from said memory element by running operating said turning mechanism, in response to receipt of said operation by said operator to said switch.

2. The X-ray imaging apparatus according to claim 1, further comprising:
a mode selection element that selects a specific imaging mode to observe a preset target region of said subject, wherein
said control element allows said table horizontal movement mechanism to move said table in said horizontal direction or causes said table horizontal movement mechanism to move said table in said horizontal direction and turns said C-shaped arm in said direction toward said-target angle by running operating said turning mechanism, in response to receipt of said operation by said operator to said switch under a condition in which said mode selection element selects said specific imaging mode.

3. The X-ray imaging apparatus according to claim 1, wherein
said control element performs turning said C-shaped arm in an opposite direction of direction toward said target angle by running said turning mechanism, when a first input power to perform said relative move of said table is provided after said turning angle of said C-shaped arm attains said target angle and said relative position of said table relative to said C-shaped arm in a long side direction of said table is in a waiting region that is outside an observation region to observe said preset target region of said subject.

4. The X-ray imaging apparatus according to claim 3, wherein
said control element performs turning said C-shaped arm in said opposite direction of direction toward said target angle, when said first input power to perform said relative move of said table is provided after a turning angle of said C-shaped arm attains said target angle;
said relative position of said table in an intermediate region between said observation region and said waiting region; and
a moving speed of said table from said observation region to said waiting region is higher than a preset value.

5. The X-ray imaging apparatus according to claim 1, wherein
said control element suspends a turning movement of said C-shaped arm by said turning mechanism when said switch provides a second input power to inhibit said relative move of said table.

6. The X-ray imaging apparatus according to claim 1, further comprising:
a horizontal axis turning mechanism that rotates said C-shaped arm around a horizontal axis, wherein
said control element turns said C-shaped arm following rotating said C-shaped arm around said horizontal axis so that said X-ray axis is parallel to said vertical axis by running said horizontal axis rotation mechanism, when said C-shaped arm turns based on a first input power that is provided to perform said relative move of said table; and said X-ray axis connecting said X-ray tube and said X-ray detector tilts relative to said vertical axis.

7. The X-ray imaging apparatus according to claim 1, wherein
said control element sets a state that allows said table to be manually movable by canceling a locked state of said table by said table horizontal movement mechanism and turns said C-shaped arm, in response to receipt of said operation by said operator to said switch.

8. The X-ray imaging apparatus according to claim 1, wherein:
said table horizontal movement mechanism includes a horizontal driving element that moves said table in said horizontal direction, wherein
said control element moves said table in said horizontal direction by running operating said horizontal driving element and turns said C-shaped arm, in response to receipt of said operation by said operator to said switch.

9. The X-ray imaging apparatus according to claim 1, further comprising:
a horizontal movement mechanism that moves said C-shaped arm in said horizontal direction, wherein
said control element moves said C-shaped arm in said horizontal direction by running operating said horizontal movement mechanism and turns said C-shaped arm, when said switch provides a first input power to move said C-shaped arm.

* * * * *